United States Patent [19]

Johnson et al.

[11] Patent Number: 4,634,673
[45] Date of Patent: Jan. 6, 1987

[54] ENZYME PURIFICATION PROCESS

[75] Inventors: Richard A. Johnson, Clinton, Iowa; Norman E. Lloyd, Ridgefield, Conn.

[73] Assignee: Nabisco Brands, Inc., Parsippany, N.J.

[21] Appl. No.: 594,188

[22] Filed: Mar. 28, 1984

[51] Int. Cl.$^4$ .............................................. C12N 9/92
[52] U.S. Cl. ................................. 435/234; 435/814; 435/816
[58] Field of Search .................. 435/234, 814, 816

[56] References Cited

U.S. PATENT DOCUMENTS 3,728,224  4/1973  Borglum ........................ 435/814 X
4,144,130  3/1979  Kula et al. ..................... 435/814 X

FOREIGN PATENT DOCUMENTS 1004613  2/1977  Canada ............................. 435/814

Primary Examiner—Lionel M. Shapiro
Attorney, Agent, or Firm—Richard Kornutik

[57] ABSTRACT

The disclosure is directed to the treatment of a glucose isomerase extract with an amine having the general formula:

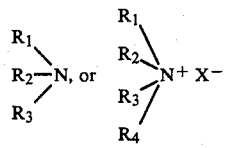

An insoluble complex containing enzyme activity is formed. The insoluble enzyme complex may be resolubilized to produce a stable concentrated and purified glucose isomerase preparation.

19 Claims, No Drawings

ENZYME PURIFICATION PROCESS

FIELD OF THE INVENTION

This invention relates to the purification of an aqueous glucose isomerase solution and particularly to the treatment of the solution with an amine to form an insoluble complex containing enzyme activity.

DESCRIPTION OF THE PRIOR ART

Glucose isomerase is an enzyme which converts glucose to fructose. Various microorganisms are known in the art which produce glucose isomerase. For example, microorganisms of the genera Actinoplanes, Aerobacter, Ampullariella, Arthrobacter, Bacillus, Lactobacillus and Streptomyces produce glucose isomerase. Generally glucose isomerase is primarily produced intracellularly and thus the major portion of the glucose isomerase is found within and/or on the cell walls of the microorganisms. Therefore, it is necessary to extract the enzyme from the microbial cells to produce the soluble enzyme. The extraction process results in at least partial disruption of the cell envelope allowing diffusion of the enzyme and other cellular materials into the microbial enzyme extract. Thus, the enzyme extract contains both soluble and insoluble impurities. The insoluble impurities can be easily separated by well known methods, such as by filtration or centrifugation. However, the soluble impurities which are believed to be biological oligomers or polymers, e.g., nucleic acids, non-enzymatic proteins or cell wall components, such as polyuronic acids and the like, are difficult and expensive to remove because they often have chemical or physical properties similar to the desired product.

Methods for removal or separation of undesirable soluble materials from microbial enzyme extracts are well known. A current summary of these methods can be found in Volume XXII of "Methods of Enzymology" pp. 273–287 and pp. 476–556 (ed. W. E. Jakoby, Academic Press, N.Y., N.Y.). Various methods for enzyme purification, such as separation based on solubility, separation based on specific affinity and chromatographic separations are described.

Numerous patents also describe various methods for purification of enzymes. U.S. Pat. No. 3,769,168 to Masuda describes the purification of beta amylase by adsorption, washing and eluting the enzyme with an ionic solution. U.S. Pat No. 3,912,595 to Philipp et al. describes the purification of a hydrolytic enzyme solution by reversibly complexing the enzyme on a granular support material in a column, after which the enzyme is recovered by elution with a buffer. U.S. Pat. No. 3,972,777 to Yamada et al. describes a method to refine β-galactosidase by selective adsorption on an acidcation exchange resin and then eluting the β-galactosidase from the resin with a buffer. All of these methods encompass contacting an impure enzyme solution with a matrix which will adsorb or bond the enzyme, and then eluting the purified enzyme from the matrix by addition of an ionic solution.

U.S. Pat. No. 4,347,322 to Johnson et al. teaches a chromatographic process for enzyme purification wherein the soluble impurities are preferentially adsorbed by an ion exchange material. In U.S. Pat. No. 4,106,992 to Vairel et al., curde urokinase is subjected to exclusion chromatography utilizing a DEAE-cellulose resin. The described process is principally directed to removing pyrogenic substances from urokinase.

Several patents teach the purification of microbial enzyme extracts by precipitation. U.S. Pat. No. 3,728,244 to Borglum teaches the precipitation of impurities with quaternary ammonium compounds. U.S. Pat. No. 3,794,562 to Bergmeyer et al. teaches the precipitation of impurities using polyethylene-imine. U.S. Pat. No. 4,055,469 to Snoke et al. teaches the precipitation of impurities using synthetic polyelelctrolytes. British Pat. No. 1,411,503 to Morisi et al. teaches the precipitation of impurities with a cationic surface active agent. All of these patents teach methods to precipitate and remove impurities while the active enzyme remains in solution.

Quaternary ammonium compounds containing at least one long chain hydrocarbon N-substituent are surface-active electrolytes which can form aggregates or micelles in solution. These compounds are characterized by the hydrophilic quaternary amino group and by the hydrophobic hydrocarbon chain. Many quaternary ammonium compounds have found wide-spread use as antimicrobial agents based on their ability to inactivate or inhibit microorganisms. This property is thought to be a result of the formation of an anion-cation complex between the positively charged quaternary amine and the negatively charged microbial surface.

Quaternary ammonium compounds also form insoluble anion-cation complexes with various negatively charged macromolecules such as proteins. Precipitation, inactivation, denaturation, redispersion and complex formation are all phenomena reported to result from the interaction of proteins with quaternary ammonium compounds.

SUMMARY OF THE INVENTION

The present invention provides a method for purification of glucose isomerase in aqueous solution. The glucose isomerase is contacted with a tertiary or quaternary amine under conditions whereby the amine interacts with the isomerase to form an insoluble enzyme-amine complex. The isomerase-amine complex may be added to a strongly ionic solution wherein the complex dissociates to produce a soluble, purified, and concentrated glucose isomerase preparation.

DETAILED DESCRIPTION OF THE INVENTION

It has been unexpectedly discovered that certain amine compounds may be used in a process to purify glucose isomerase preparations.

The tertiary and quaternary amine compounds that can be used in the present method are represented by the following formula:

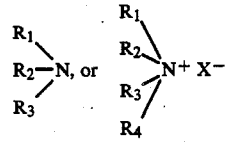

where
R$_1$ is a hydrocarbyl radical containing at least 6 carbon atoms,
R$_2$ is a hydrocarbyl radical containing from about 8 to 20 carbon atoms,
R$_3$ is lower alkyl, and R$_4$ is hydrogen or lower alkyl.

The hydrocarbyl radicals are preferably alkyl, cycloalkyl, alkene, aryl, and aralkyl, and may be substituted by such groups as halide, e.g., chloro and bromo, hydroxy, alkoxy and the like. The hydrocarbyl radicals are also intended to include hydrocarbon chains interrupted by oxygen or sulfur atoms, as in ether or thioether linkages, e.g., diisobutylphenoxyethoxyethyl and diisolbutylcresoxyethoxyethyl radicals.

X may be any suitable inorganic or organic anion, such as a halide, nitrate, sulfate, benzenesulfonate, acetate, etc., the anion being inert to the enzyme.

Exemplary of amine groups represented by the above formula which may be used in the process of the invention are dimethylbenzyldodecyl ammonium, dimethyldilauryl ammonium, stearyldimethylbenzylammonium, distearyldimethylammonium, diethyldioctadecyl ammonium, dimethyldidodecyl ammonium, dimethyldodecylnaphthylmethyl ammonium, dimethylhexadecyldichlorobenzyl ammonium, and dimethyldiisobutylphenoxyethylbenzyl ammonium salts.

In accordance with the present invention at least one of the above described amine compounds is added to the glucose isomerase aqueous extract to be purified under conditions such that the amine interacts with the glucose isomerase to form an insoluble isomerase-amine complex which precipitates. The insoluble isomerase-amine complex is then separated by normal means such as filtration, centrifugation or the like. To remove the enzyme from the precipitate, the isomerase-amine complex is added to an ionized salt solution wherein the complex dissociates and the isomerase and amine resolubilize. The amine compound may then be separated from the enzyme solution by ultrafiltration, or by treatment with cation exchange resin, to produce a purified, concentrated glucose isomerase preparation having a high specific activity (e.g., activity per mg protein).

The amount of ionized salt required for the re-dissolution of the precipitated enzyme-amine complex can be readily determined by simple test procedures using solutions of varying concentration, i.e., ionic strength, of suitable electrolytes of which sodium chloride is preferred because of economy and availability. Any electrolyte can be used as long as it does not adversely affect the glucose isomerase. The requisite amount of salt will be determined as the minimum concentration required to dissolve the precipitate. Since sodium chloride does not seem to have any noticeable effect on the enzyme, it can be used in concentrated solution to assure complete dissolution of the precipitate.

In some cases, the aqueous enzyme solution from which the enzyme is to be recovered may contain impurities which do form precipitates with the added amine compound prior to precipitating the desired enzyme. In such cases, the addition of amine should be in several stages, usually two stages, in the first of which the impurities are precipitated out and finally the enzyme in the second stage. The amount of amine needed for the first stage is readily determinable using aliquots of the original enzyme solution to which is added graduated amounts of amine compound. The precipitate formed at each addition is tested for enzyme activity which once detected indicates the amount of precipitant necessary for the first stage precipitation.

In practicing the present invention it is preferred to use quaternary amines of the above general formula wherein $R_2$ is an alkyl radical containing from about 8 to about 18 carbon atoms, $R_1$ is a radical containing from about 6 to about 10 carbon atoms, $R_3$ and $R_4$ are lower alkyl and X is a halide anion. The more preferred compounds are those wherein $R_2$ is an alkyl radical having from 12 to 18 carbon atoms, $R_1$ is an aralkyl radical having from 7 to 10 carbon atoms, $R_3$ and $R_4$ are lower alkyl radicals and X is a halide radical.

The most preferred compounds may be represented by the following formula:

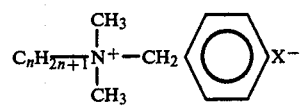

where n is an integer equal to 12, 14, or 16 and X is a halide anion. A product containing these compounds is sold under the name of BTC-835 by Onyx Chemical Co., Jersey City, N.J. BTC-835 is a mixture composed of 50% of a compound where n in the above formula is 14, 40% of a compound where n in the above formula is 12, and 10% of a compound where n in the above formula is 16.

The conditions contemplated for performing the instant invention may vary depending on the purity and concentration of the isomerase extract and the particular amine compound utilized. The amount of amine used should be sufficient to precipitate substantially all of the active enzyme and will generally be at least 100 ppm, on a weight per volume basis. The preferred amount is at least about 500 ppm and usually from about 500 ppm to about 5,000 ppm. The most preferred is from about 1,000 to about 3,000 ppm.

The pH should be within the range that is about one pH unit above the isoelectric point (pI) of the enzyme and about one pH unit below the pKa of the amine compound utilized. Preferably, the pH is at a value of from about 5.5 to about 8.5, ideally from about 6.0 to about 8.0 and most preferably from about 7.0 to about 7.4.

The temperature may vary over a wide range from as low as 0° C. up to below the temperature at which heat denaturation or inactivation of the enzyme occurs. For convenience the process will generally be conducted at ambient temperature.

The mechanism of the present process is not completely understood. However, it is believed that the amine interacts with the glucose isomerase to form an insoluble isomerase-amine complex. When the insoluble isomerase-amine complex is added to a highly ionic solution, the isomerase-amine complex dissociates and the isomerase and amine are again soluble.

The results obtained with the present invention are unexpected. It was very surprising that the present amine compounds which are generally believed to be potent enzyme inactivators and denaturizing agents can be used to purify glucose isomerase extracts. Surprisingly, not all quaternary ammonium salts nor all tertiary amines are capable of providing the results obtained using the specified tertiary amines and quaternary ammonium salts of the present invention. Known quaternary amine salts such as hexadecyltrimethyl ammonium chloride, formed no precipitate under conditions of the present invention, while other amine compounds, e.g., octadecyltrimethylammonium chloride, formed a slight precipitate which showed no detectable enzyme activity. Other amines caused significant loss of enzyme activity whether precipitate formed or not. The especially effective amine compounds are those wherein $R_1$ is an aralkyl group of from 7-10 carbon atoms, eg., benzyl and naphthylmethyl, $R_2$ is alkyl of from 12 to 16 carbon atoms, and $R_3$ and $R_4$ are each lower alkyl, especially methyl. It was also surprising that the isomerase-amine complex could be dissociated so easily to produce a purified active enzyme.

Methods to produce the glucose isomerase extracts used as starting materials in the process of the present invention are well known in the art. For example, an enzyme extract containing glucose isomerase may be obtained by fermentations of microorganisms of a species known to produce glucose isomerase, extracting the enzyme from the mycelia and removing insoluble material by known methods.

The preferred glucose isomerase extracts may be obtained from microorganisms of the genera Actinoplanes, Ampullariella, Aerobacter, Arthrobacter, Bacillus, Micromonospora, Microbispora, Microellobospora, Norcardia, or Streptomyces. Glucose isomerase extract typically may be obtained from microorganisms of the species *Streptomyces rubigenosus, Streptomyces olivochromogenes, Bacillus coagulans* or *Bacillus stearothermophilus.*

ANALYTICAL METHODS

Total Protein

Total protein was determined employing a Beckman Model DK—2A Spectrophotometer at a wavelength of 280 millimicrons.

Isomerase Activity—IGIU

IGIU is the abbreviation for International Glucose Isomerase Unit and is that amount of enzyme which will convert 1 micromole of glucose to fructose per minute in a solution initially containing 2 moles of glucose per liter, 0.02 moles of $MgSO_4$ and 0.001 moles of $CoCl_2$ per liter at a pH of 6.84 to 6.85 (0.2M sodium maleate) measured at ambient temperature, and at a temperature of 60° C. Glucose isomerase determinations were carried out by the method described by N. E. Lloyd et al., Cereal Chem,. 49, No. 5 pp. 544-553 (1972).

Immobilized Isomerase Activity-FAU

Immobilized isomerase activity was determined by the following procedure.

An immobilized isomerase sample containing 1400–2200 IGIU was weighed out. The sample was washed into a 250 ml flask with 125 ml dextrose assay solution (previously warmed to 65° C.) and 10 ml of 0.1 tris-hydroxymethylamino-methane (THAM) solution (pH 7.8). Dextrose assay solution contained 3.33M dextrose, 20 mM magnesium sulfate, 10 mM sodium sulfite, 100 mM THAM and 1 mM cobalt chloride (pH 7.8). At 65° C. this dextrose solution has a pH value of 7.0. The flask was immersed in a 65° C. water bath and shaken for 1 hour. The mixture was vacuum-filtered through a 45 mm coarse fritted glass funnel fitted with a glass fiber filter and precoated with 1 g of filter-aid. The flask and enzyme cake were rinsed with small aliquots of 100 mM THAM buffer solution (pH 7.8) totaling 100 ml.

This washed enzyme was added to a 250 ml flask containing 125 ml dextrose assay solution (previously equilibrated to 65° C.). The washed enzyme was quantitatively washed into the flask with 10 ml of 10 mM THAM buffer (pH 7.8), and the flask was shaken for exactly 60 minutes. 12.0 ml glacial acetic acid was then added, and the acidified mixture shaken for a further 15 minutes. The mixture was vacuum-filtered through a 45 mm coarse fritted glass funnel fitted with a glass fiber filter and precoated with approximately 1 g filter-aid. The flask and the funnel contents were washed with demineralized water until approximately 400 ml of filtrate was collected. The filtrate cooled to 25° C. was diluted to 500 ml. The rotation of the solution was determined with a 2 dm cell at 25° C. as $R_2$.

A blank was processed in the same manner as above, except no enzyme was added. The optical rotation of the blank was also determined at 25° C. as $R_1$. The degree of isomerization is calculated from the following relationship:

$$I = \frac{(R_2 - R_1)}{aC_pL}$$

where a is the specific rotation change when fructose is completely converted to dextrose, $C_p$ is the concentration of sugar in solution (0.15 g/ml), and L is length of polarimeter tube (2 dm).

Fixed activity units (FAU) of the isomerase activity is calculated as follows:

$$FAU/g = JC/K_f tw$$

where $K_f$ is a rate constant (1.21 l hr$^{-1}$FAU$^{-1}$ mg glucose), t is the reaction time in hours (1 hr.), w is the weight in g of the sample, C is the initial concentration in mg per 125 ml reaction mixture (75,000 mg glucose), and J is defined as follows:

$$J = \left[ I_e\left(\frac{K_s}{C_m} + 1\right) + I_e^2\left(\frac{K_s}{K_p} - 1\right) \right] \ln\left(\frac{I_e}{I_e - I}\right) - I_e I\left(\frac{K_s}{K_p} - 1\right)$$

where
$I_e$ = degree of isomerization at equilibrium in mole fraction of fructose (0.513).
I = degree of isomerization in mole fraction of fructose.
$C_m$ = initial molar concentration of glucose (3.33M).
$K_s$ = Michaelis constant for glucose (0.7M).
$K_p$ = Michaelis constant for fructose (1.43M).
One IGIU is equal to 15.8 FAU's.

The following examples further illustrate the invention.

EXAMPLE 1

This example illustrates the formation of an insoluble glucose isomerase-amine complex and then dissociation of the complex in an ionic solution to produce a purified active glucose isomerase preparation.

A glucose isomerase extract was obtained from microorganisms of a selected strain of the Streptomyces genus and adjusted to pH 7.2. The isomerase activity of the extract was 40 IGIU/ml. To each of nine containers was added 25 ml of the enzyme extract (1,000 IGIU—Total). An appropriate amount of BTC—835, N—alkyl($C_{12}$, $C_{14}$, $C_{16}$)—dimethyl-benzyl ammonium chloride, Onyx Chemical Co., Jersey City, N.J.) was added to each container at room temperature with continuous stirring for 15 minutes. The addition of the BTC resulted in the formation of a white flocculant precipitate, even at the lowest level of 100 ppm.

The precipitates were removed by centrifugation and portions of the resulting supernates were assayed for isomerase activity. The results are summarized in Table I.

TABLE 1

| Trial | [BTC] ppm | Soluble Activity IGIU/ml | % Remaining Supernatant Fraction |
|---|---|---|---|
| 1 | 0 | 40 | 100 |
| 2 | 100 | 40 | 100 |
| 3 | 500 | 20 | 50 |
| 4 | 1000 | 0 | 0 |
| 5 | 1500 | 0 | 0 |
| 6 | 2000 | 0 | 0 |
| 7 | 3000 | 0 | 0 |
| 8 | 4000 | 0 | 0 |
| 9 | 5000 | 0 | 0 |

The data show that no soluble isomerase activity remained at a BTC concentration of 1000 ppm or more. At a BTC concentration of 500 ppm the remaining soluble activity was 50%.

The precipitate from trial 5 was resuspended in 5 ml of 0.5N NaCl at room temperature and stirred. The precipitate redissolved in a few minutes. A 0.5 ml portion of the resulting solution was diluted with 19.5 ml of 0.5N NaCl and assay showed isomerase activity.

EXAMPLE 2

This example illustrates the use of the invention process to produce a purified and concentrated glucose isomerase.

A 300 ml sample of the isomerase extract of Example 1, having a total activity of 12,000 IGIU and a specific activity of 2.7 IGIU/mg protein, was adjusted to pH 7.2 with NaOH. BTC-835 was added to give a final concentration of 1000 ppm and stirred for 15 minutes. The precipitate that formed was collected by filtration on a precoat of filter aid. The filter cake was washed on the filter with water and samples of the filtrate and washings were assayed for isomerase activity. No soluble activity was detected.

The filter cake was eluted with 0.5N NaCl. The sodium chloride eluate was ultrafiltered with an Amicon 401 stirred cell (Amicon Corp., Danvers, MA) using an XM100 [(100,000 Mol. Wt. cut-off (MWCO)] membrane. The ultrafilter retentate was diafiltered with three 5-volume portions of 0.5N NaCl to remove residual unbound BTC. Finally the retentate was desalted by repeated diafiltration with water. The final retentate contained a total of 8860 IGIU with a specific activity of 43.32 IGIU/mg protein. A total of 73.8% of the starting isomerase activity was recovered and the specific activity of 43.32 IGIU/mg protein indicated that the preparation was at least 90% isomerase on a protein basis. Thus, a purification of about 20 fold was achieved with good recovery of activity.

EXAMPLE 3

The procedure of Example 2 is repeated using an isomerase extract obtained from a second fermentation of the same Streptomyces described in Example 1.

A 500 ml portion of the isomerase extract (14,000 IGIU total) was adjusted to pH 7.2 and BTC-835 was added dropwise to a final concentration of 1000 ppm. The resulting suspension was filtered after admixing 2 g of filter aid and the filter cake was washed with about 100 ml of water. The filtrate plus washings contained no isomerase activity. The washed filter cake was then slowly eluted in situ with 300 ml of 0.5N NaCl over a 3 hour period.

The salt eluate was ultrafiltered with an Amicon XM-50 (50,000 MWCO) membrane. The ultrafilter retentate was diafiltered extensively with 0.5N NaCl and then with water to remove residual BTC and salt. The final retentate contained a total of 13,550 IGIU with a specific activity of 43.4 IGIU/mg. Thus, the purification was as efficient as in Example 2 and the recovery of activity (94%) was significantly improved.

EXAMPLE 4

This example illustrates the process of the invention to purify an isomerase extract obtained from a Bacillus microorganism.

A. The starting enzyme source was a dry powder consisting of Bacillus whole cells mixed with a filter aid carrier and identified as Novo SP-103 isomerase (Novo Industri A/S, Bagsvaerd, Denmark). Enzyme solubilization was accomplished by suspending the powder in dilute Tris buffer, pH 7.0, and stirring for two hours at room temperature after the addition of lysozyme (200 mg/100 g dry enzyme). Insoluble material was then removed by filtration through a filter aid precoat and the filtrate was heated to 60° C. and held for 20 minutes to precipitate impurities and pasteurize the extract. After removal of insolubles by precoat filtration a 10 ml portion of the extract (262 IGIU) was adjusted to pH 7.2 and BTC-835 was added to a final concentration of 1500 ppm. The heavy white precipitate which formed almost immediately was removed by centrifugation, and an aliquot of the supernate was assayed for isomerase activity. Virtually all of the starting activity (250 IGIU) was present in the soluble fraction.

B. A portion of the original extracts from part A was treated with 1500 ppm BTC-835, and the resulting insoluble material was removed by filtration and discarded. 25 ml portions (555 IGIU, each) of the treated extract were then used for the addition of various amount of BTC-835 to determine what concentration would be necessary to precipitate isomerase. After addition of the BTC, precipitates were removed by centrifugation and aliquots of the soluble phase were assayed for isomerase activity. The results are summarized in Table II.

TABLE II

| Trial | [BTC] ppm | Soluble Activity IGIU/ml | Soluble Activity Total IGIU | % Soluble (555 IGIU Total) |
|---|---|---|---|---|
| 1 | 1000 | 10.36 | 259 | 46.6 |
| 2 | 2000 | 1.76 | 44 | 7.9 |
| 3 | 3000 | 1.76 | 44 | 7.9 |
| 4 | 5000 | 2.10 | 53 | 9.5 |

Addition of BTC, after pretreatment with 1500 ppm to remove the nonenzyme impurities, resulted in almost complete loss of soluble isomerase activity at concentrations of 2000 ppm BTC or higher. An addition of 1000 ppm resulted in precipitation of about half of the soluble activity.

The precipitate from each of the above trials was suspended in 10 ml of 0.5N NaCl. The precipitates redissolved radidly. The solutions containing the dissolved precipitates were pooled and ultrafiltered with an XM-50 membrane. After diafiltration with 0.5N NaCl and with water, the retenate was analyzed for isomerase activity and protein concentration. Total recovery of activity was 1103 IGIU. The specific activity was 4.16 IGIU/mg based on protein estimation by U.V. absorbance.

EXAMPLE 5

This example illustrates the treatment of a glucose isomerase extract with various quaternary ammonium compounds.

Equal portions of the isomerase extract described in Example 3 were adjusted to pH 7 and the various quaternary ammonium compounds were added to a final concentration of 2000 ppm. Formation of a precipitate was taken as evidence of an interaction between the enzyme and the quaternary ammonium compound.

The following quaternary compounds were tested:
1. BTC-835
   Alkyl ($C_{12}$, $C_{14}$, $C_{16}$) dimethylbenzyl ammonium chloride
2. ARQUAD 18-50
   Octadecyltrimethyl ammonium chloride
3. CERTRIMIDE (CTAB)
   Cetyltrimethyl ammonium bromide
4. BTC-2125M (DUAL QUAT)
   Alkyl ($C_{14}$, $C_{16}$, $C_{12}$, $C_{18}$) dimethylbenzyl ammonium chloride
   Alkyl ($C_{12}$, $C_{14}$) dimethylethylbenzyl ammonium chloride
5. HYAMINE 1622
   Diisobutylphenoxyethoxyethyldimethylbenzyl ammonium chloride
6. HYAMINE 2389
   (Methyldodecylbenzyl)trimethyl ammonium chloride Methyldodecylxylenebis(tetramethyl)ammonium choride
7. MAQUAT DLC 1214
   Alkyl ($C_{12}$, $C_{14}$, $C_{16}$, $C_{18}$) dimethyl(dichlorobenzyl)ammonium chloride
8. BTC-812
   Octyldodecyldimethyl ammonium chloride
9. Hexadecyltrimethyl ammonium chloride Compounds 1, 4, 5 and 7 formed copious white precipitates; less precipitation occured with 8, 3 and 2, while 9 and 6 remained clear. The suspensions were centrifuged to sediment out the precipitates, and aliquots of the clear supernates were assayed for isomerase activity.

The precipitates were resuspended in 0.5N NaCl to dissociate the enzyme-quaternary ammonium compound complex and resolubilize the enzyme. Aliquots of the resolubilized precipitates were assayed for isomerase actitity after dilution with 0.5N NaCl —0.2M $Co^{++}$.

The results are summarized in Table III.

TABLE III

| Compound Number | ppt. | Soluble Activity IGIU | Recovered ppt. Activity IGIU | Total IGIU |
|---|---|---|---|---|
| 1 | +++ | 101 | 1422 | 1523 |
| 2 | + | 1772 | — | 1772 |
| 3 | + | 664 | — | 664 |
| 4 | +++ | 58 | 278 | 336 |
| 5 | +++ | 182 | 722 | 904 |
| 6 | — | 1820 | — | 1820 |
| 7 | +++ | 8 | 272 | 280 |
| 8 | ++ | 1064 | 722 | 1786 |
| 9 | — | 1974 | — | 1974 |
| Control | — | 1980 | — | 1980 |

The four compounds that gave the most abundant visible precipitation, numbers 1, 4, 5 and 7, all contain the N-benzyl substituent.

BTC-812 (8), which contains two long chain alkyl groups, resulted in a precipitate which was physically different from BTC-835 and other precipitates. Recovery of activity in this case was excellent. Compounds 6 and 9 caused no obvious precipitation and very little enzyme inactivation. Compounds 3, 4, and 7 caused significant losses of activity.

EXAMPLE 6

This example illustrates that the insoluble complex of an enzyme and a quaternary ammonium compound is enzymatically active.

A sample of the isomerase extract of Example 4 was adjusted to pH 7.2, treated to attain a level of 1500 ppm BTC-835, admixed with filter aid and the insoluble material collected by filtration. The filter cake was washed with water and blended. A sample was analyzed for immobilized enzyme activity by the FAU procedure.

The results showed an expressed activity that was 29% of the starting soluble activity.

EXAMPLE 7

This example describes an alternative procedure using a strong acid cation exchange resin to remove BTC from redissolved isomerase BTC precipitates. A partially purified isomerase concentrate was prepared by ultrafiltration of a crude enzyme extract with an Amicon CH4 concentrator using an HIP100 cartridge (100,000 MWCO). The ultrafilter retentate was diafiltered with 5 volumes of deionized water to remove residual low molecular weight solubles. The final concentrate had a potency of 2175 IGIU/ml and a protein concentration of 66.9 mg/ml. (Specific Activity 32.5 IGIU/mg)

A 10 ml portion of this concentrate was diluted to 300 ml with water and the pH was adjusted to 7.2. To this solution was added 300 mg of BTC-835 and the suspension was stirred 30 minutes. The precipitate which formed was collected by centrifugation and redissolved in 25 ml of 0.5M NaCl. To this solution was added 1 g d.b. of moist AG50 W X4 (manufactured by Bio Rad Laboratories, Richmond, CA) cation exchange resin (sodium form). The pH was adjusted to 7.0 and the suspension was stirred gently for 30 minutes. The resin was then allowed to settle and an aliquot of the supernate was taken for U.V. analyses for soluble protein (absorbance at 280 nm.) and BTC (absorbance at 262 nm.) The U.V. analyses showed total removal of soluble BTC. An additional aliquot of the supernate was taken and diluted 10 fold with water. The absence of a precipitate at this reduced salt concentration indicated that the BTC had been removed by the resin. The remainder of the supernate was separated from the resin by filtration and the filtrate was ultrafiltered with an Amicon 201 stirred cell using a YM-30 membrane to separate residual NaCl. The final ultrafilter retentate was assayed for isomerase activity and protein concentration. Recovery of isomerase activity was 19,400 IGIU or more than 90% of the starting activity when corrected for sampling losses. The specific activity was 40.12 IGIU/mg protein.

EXAMPLE 8

This example illustrates the use of various quaternary and tertiary amines in the process of the invention. The experimental procedure was essentially the same as described in Example 5. Successful enzyme precipitation and recovery of at least 80% of the precipitated activity was achieved with the following compounds:

MAQUAT MC 1412
  Alkyl ($C_{14}$, $C_{12}$, $C_{16}$) dimethylbenzyl ammonium chloride
BTC-1010
  Didecyldimethyl ammonium chloride
BTC-1100
  Alkyl ($C_{12}$, $C_{14}$) dimethyl 1-napthylmethyl ammonium chloride
  Stearyldimethylbenzyl ammonium chloride
HYAMINE 3500
  Alkyl ($C_{14}$, $C_{12}$, $C_{16}$) dimethylbenzyl ammonium chloride Either no enzyme precipitated, or inactivation occurred when the following compounds were used:

VARIQUAT B-200
  Benzyltrimethyl ammonium chloride
ARQUAD 12-50
  Dodecyltrimethyl ammonium chloride
  Dimethyldodecyl amine
  Dimethylbenzyl amine
  Triisooctyl amine

What is claimed is:

1. A process for separating glucose isomerase values from aqueous solution which comprises contacting said aqueous solution with an amine compound of the formula

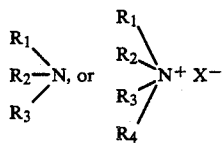

wherein:
  $R_1$ is a hydrocarbyl radical of at least 6 carbon atoms;
  $R_2$ is a hydrocarbyl radical of from about 8 to about 20 carbon atoms;
  $R_3$ is lower alkyl;
  $R_4$ is H or lower alkyl; and
  X is an anion;
and recovering the enzyme-containing precipitate thus produced.

2. The process according to claim 1 wherein the pH of said solution is from about 5.5 to about 8.5.

3. The process according to claim 1 wherein the amount of the amine compound is at least 500 ppm of said aqueous solution.

4. The process according to claim 1 wherein the pH is from about 6 to about 8.

5. The process according to claim 1 wherein in the amine compound $R_1$ is alkyl of from about 8 to about 18 carbon atoms, $R_2$ is a hydrocarbyl radical of from about 6 to about 10 carbon atoms, $R_3$ and $R_4$ are each lower alkyl and X is a halide anion.

6. A process for separating glucose isomerase values from aqueous solution which comprises contacting said aqueous solution with an amine compound formula:

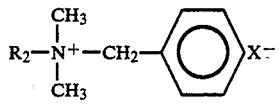

wherein $R_2$ is $C_nH_{2n+1}$
in which n is an integer equal to 12, 14 or 16, and X is an anion, and recovering the enzyme-containing precipitate thus produced.

7. The process according to claim 6 wherein the pH of said solution is from about 5.5 to about 8.5.

8. The process according to claim 6 wherein the amount of the amine compound is at least 500 ppm of said aqueous solution.

9. The process according to claim 6 wherein the pH is from about 6 to about 8.

10. The process according to claim 6 wherein $R_2$ is a mixture of radicals of the formula $C_nH_{2n+1}$ wherein n is 12, 14 and 16.

11. The process according to claim 6 wherein the pH of said aqueous solution is from about 7.0 to about 7.4.

12. The process according to claim 6 wherein the amount of said amine compound is at least 1000 ppm of said aqueous solution.

13. The process according to claim 1 including the further step of redissolving the separated enzyme-containing precipitate in an aqueous medium.

14. The process according to claim 6 including the further step of redissolving the separated enzyme-containing precipitate in an aqueous medium.

15. The process according to claim 14 wherein the aqueous medium comprises an ionized salt.

16. The process according to claim 6 wherein the amine compound is alkyl ($C_{12}$, $C_{14}$, $C_{16}$) dimethylbenzyl ammonium chloride.

17. The process according to claim 1 wherein the amine compound is octyldodecyldimethyl ammonium chloride.

18. The process according to claim 1 wherein the amine compound is stearyldimethylbenzyl ammonium chloride.

19. The process according to claim 1 wherein the amine compound is didecyldimethyl ammonium chloride.

* * * * *